US012727865B2

(12) United States Patent
Ayagh

(10) Patent No.: US 12,727,865 B2
(45) Date of Patent: Sep. 8, 2026

(54) MEDICAL DEVICE FOR CONDUCTING PAPANICOLAOU (PAP) TEST

(71) Applicant: Kamran Ayagh, Alpharetta, GA (US)

(72) Inventor: Kamran Ayagh, Alpharetta, GA (US)

(73) Assignee: PapEasy, Inc., Norcross, GA (US)

(*) Notice: Subject to any disclaimer, the term of this patent is extended or adjusted under 35 U.S.C. 154(b) by 755 days.

(21) Appl. No.: 17/147,746

(22) Filed: Jan. 13, 2021

(65) Prior Publication Data

US 2022/0218318 A1 Jul. 14, 2022

(51) Int. Cl.

| | |
|---|---|
| ***A61B 1/00*** | (2006.01) |
| ***A61B 1/04*** | (2006.01) |
| ***A61B 1/06*** | (2006.01) |
| ***A61B 1/303*** | (2006.01) |
| ***A61B 10/02*** | (2006.01) |
| ***A61B 10/04*** | (2006.01) |
| ***G16H 10/40*** | (2018.01) |
| ***G16H 10/60*** | (2018.01) |
| ***G16H 20/40*** | (2018.01) |
| *A61B 10/00* | (2006.01) |

(Continued)

(52) U.S. Cl.

CPC .......... *A61B 10/04* (2013.01); *A61B 1/00124* (2013.01); *A61B 1/00135* (2013.01); *A61B 1/00154* (2013.01); *A61B 1/04* (2013.01); *A61B 1/0684* (2013.01); *A61B 1/303* (2013.01); *G16H 10/40* (2018.01); *G16H 10/60* (2018.01); *G16H 20/40* (2018.01); *A61B 2010/0003* (2013.01); *A61B 2010/0216* (2013.01); *A61B 2090/034* (2016.02); *A61M 2025/0037* (2013.01)

(58) Field of Classification Search

None

See application file for complete search history.

(56) References Cited

U.S. PATENT DOCUMENTS 4,235,244 A * 11/1980 Abele .................... A61B 10/04 600/572

5,867,821 A * 2/1999 Ballantyne ............. G16H 70/60 709/217

(Continued)

FOREIGN PATENT DOCUMENTS

WO WO 2019094948 5/2019

*Primary Examiner* — Tse Chen

*Assistant Examiner* — Martin Nathan Ortega

(74) *Attorney, Agent, or Firm* — FALATI

(57) ABSTRACT

A medical device for conducting papanicolaou (pap) test is disclosed. The device comprises a protective guide, an endoscopic device, a cell extraction device, and a computing device. The protective guide has an upper chamber and a lower chamber. The endoscope has a camera and a light emitting device assembly. The endoscope is securely positioned within the upper chamber. The cell extraction device has a handle at one end and a brush affixed at another end. The cell extraction device is slidably positioned within the lower chamber. The cell extraction device is configured to slide outward for positioning the brush around the user's cervix, thereby conveniently allowing for a cervical cell sample to be collected. The computing device in communication with the endoscope device and is configured to improve detection accuracy and visual examinations of the targeted cervical area, thereby enabling the user to collect the cervical cell sample for conducting the PAP test.

14 Claims, 5 Drawing Sheets

(51) Int. Cl.
*A61B 90/00* (2016.01)
*A61M 25/00* (2006.01)

(56) References Cited

U.S. PATENT DOCUMENTS

| | | | | |
|---|---|---|---|---|
| 6,336,905 | B1 * | 1/2002 | Colaianni | A61B 10/0291 600/569 |
| 2003/0004755 | A1 * | 1/2003 | Basch | G06F 40/174 705/2 |
| 2003/0181823 | A1 * | 9/2003 | Gatto | A61B 1/3132 600/564 |
| 2008/0188769 | A1 * | 8/2008 | Lu | A61B 10/02 600/569 |
| 2009/0203966 | A1 * | 8/2009 | Mizuyoshi | A61B 1/00096 600/182 |
| 2014/0107496 | A1 * | 4/2014 | Hellstrom | A61B 5/0086 600/478 |
| 2014/0236635 | A1 * | 8/2014 | Liberty | G16H 10/60 705/3 |
| 2015/0182205 | A1 | 7/2015 | Millard et al. | |
| 2017/0273716 | A1 | 9/2017 | Garofalo | |
| 2019/0208641 | A1 * | 7/2019 | Yates | A61B 5/0538 |
| 2019/0231177 | A1 | 8/2019 | Dreyer | |
| 2020/0185071 | A1 * | 6/2020 | Luber | G16H 50/20 |
| 2020/0237452 | A1 * | 7/2020 | Wolf | G06F 3/048 |
| 2022/0061650 | A1 * | 3/2022 | Tingvatn | A61B 1/303 |

* cited by examiner

MEDICAL DEVICE FOR CONDUCTING PAPANICOLAOU (PAP) TEST

BACKGROUND OF THE INVENTION

Cancer is a leading cause of death in the United States. Cervical cancer is the second most common cause of cancer-related mortality in women worldwide. Cervical cancer often has a poor prognosis, even when diagnosed early, and signs and symptoms may not appear until the cancer is quite advanced and complete surgical removal is not possible. The 5-year survival rate of the cervical cancer is about 80% or more if the cancer is detected early, the survival rate is increased.

Human Papillomavirus (HPV) is present in 99.7% of cervical cancer patients. Epidemiological and laboratory studies suggest a key role for human papillomavirus (HPV) in cervical carcinogenesis. However, HPV infection alone is not sufficient for cervical carcinogenesis. Most HPV infections resolve spontaneously, but if an oncogenic (high risk) HPV infection persists, there may be progression to a high-grade cervical dysplasia or cervical cancer.

The most common method for diagnosing infection of the HPV is a cervical Papanicolaou smear (hereinafter, a Pap smearing test) that performs a cell diagnostic test by using the eliminated cells obtained from the cervix. This Papanicolaou (Pap) smear has become the most commonly used method to screen for cervical dysplasia. It has been a success and the incidence of cervical cancer has been dramatically reduced. However, cytology screening programs have limitations, especially limited sensitivity, and repeated tests are therefore necessary.

The Papanicolaou test (also called Pap smear, Pap test, cervical smear, or smear test) is a screening test used to detect potentially pre-cancerous and cancerous processes in the endocervical canal (transformation zone) of the female reproductive system. The PAP smear is an important routine gynecological test, usually done in females to detect and screen for potentially precancerous and cancerous processes in the cervix (opening of the uterus or womb) or colon.

Each year about a quarter million of women around the world die from cervical cancer. Women who don't get routine pap tests experience a greater risk for developing cervical cancer. Nearly 90% of cervical cancer deaths occur in less developed regions where access to medical testing and care is limited. The world health organization (WHO) and cancer association encourage easier and more affordable methods to be offered. However, many women with access are still avoiding this potentially lifesaving test due to many various issues.

Medical diagnostic testing methods are critical screening tools for the early detection of pathological conditions. Early detection permits the identification of such conditions at a stage when successful treatment is more likely. Early treatment also frequently involves less damaging or less invasive treatment methods and decreases the impact on the patient. In addition to routine screening, diagnostic testing is also used in a variety of other applications, including biopsy analysis and monitoring the results of ongoing medical treatment.

One particularly useful tool in diagnostic testing is the Papanicolaou staining process. This process was first developed for the staining of gynecological specimens, and has led to a dramatic decrease in the fatality rate from cervical cancer. The tests known in the art typically require an in-office visit with a gynecologist where the doctor takes a sample of the cervix for lab analysis. Current medical practice requires a gynecologist for performing the pap-test using medical devices such as a speculum. The gynecologist inserts the speculum into the patient's vagina to access the cervix for tissue sample collection. Many women find this method an uncomfortable, intrusive exam, and opt to not have the routine screening performed. The existing method makes the experience very painful, uncomfortable, and is awkward. Moreover, the existing pap-test procedures are not capable of any form of mobile or self-testing options, and are generally expensive for the patients.

As stated above, the prior art method of conducting a pap smear involves the use of a speculum to spread and open the patient's vagina. The utilization the speculum could be extremely uncomfortable and painful to many patients as the vagina is spread apart. Some women have even described the speculum as agonizing and the fear and apprehension associated with the speculum has unfortunately caused many women to delay the pap smear test, or in some cases to even avoid it entirely. This is unacceptable because it could allow preventable cancer to remain undiagnosed.

A few devices and methods exist for enabling the patient to perform self-test for screening and detecting potentially precancerous and cancerous processes in the cervix (opening of the uterus or womb) or colon. However, the existing devices and methods are major limitations, including, for example, failure to provide proper visualization, digital guidelines, and instructions. Further, the existing devices and methods are not suitable for less developed countries and also do not provide flexibility and are generally bulky in diameter and difficult to use and experience by the patient.

Henceforth, there is a need for a medical device and method for enabling a woman to simply and conveniently collect a personal cervical cell sample for use during a Papanicolaou (PAP) test or PAP smear. There is also a need for an efficient and inexpensive medical device and method for enabling a woman to privately perform the PAP test, without the need for assistance from a gynecologist or other medical practitioner. Further, there is also a need for an efficient and inexpensive medical device and method used to detect cervical cancer, chlamydia, gonorrhea, and HPV. In addition, there is a need for newer, unique, and revolutionary methods of pap-test using the medical device of the present invention.

SUMMARY OF THE INVENTION

The present invention discloses a gynecological medical device. The present invention further discloses a medical device for enabling a woman to simply conduct a Papanicolaou (PAP) test by conveniently collecting a cervical cell sample, without the need for assistance by a gynecologist or other medical practitioner. In one embodiment, the medical device is a mobile or portable self-testing medical device. The mobile capability of the medical device, offered to less or underdeveloped for medical professional and world health associations, provides mass testing without the need of necessary expensive, difficult, and painful examination setups and equipment, and hard to access testing locations and procedures.

As such, the present invention is configured to provide a self-testing kit that allows all medical professional offices to offer the pap-test with considerations that it be beneficial, economical, and more accessible. The self-testing kit can be a mobile device, which could allow medical professionals and users to conduct the pap-test without restricting the testing be done by Gynecologists, thereby allowing accessibility and ease of use and ultimately mass testing procedure.

In one embodiment, the device comprises a protective endoscopic catheter or protective guide, an endoscopic device, a cell extraction device, and a computing device. In one embodiment, the protective guide is a disposable dual-chambered tube. In one embodiment, the protective guide has a maximum external diameter of less than 1 cm and is configured to reduce the overall diameter to help with the discomfort of larger size tubing inserted into the vaginal channel. In one embodiment, the protective guide comprises an upper chamber and a lower chamber. In one embodiment, the upper chamber has a lip stopper. The lip stopper could allow an average finger to be inserted vertically, instead of a round tubing of the same larger diameter. In one embodiment, the protective guide has a dimension of about 7 mm width. In one embodiment, the protective guide has a dimension of about 13.5 mm to about 14 mm height. The protective guide has a diameter of about 14 mm or significantly higher all around the shape.

In one embodiment, the endoscope device comprises a camera and a light emitting device assembly. The light emitting device assembly comprises one or more light emitting diodes (LEDs). In an exemplary embodiment, the light emitting device comprises at least 4 LEDs. In one embodiment, the one or more light emitting diodes are configured to produce illumination for the camera through the endoscope to acquire video and/or image data of the user's cervical area. In one embodiment, the lip stopper is configured to stop the endoscopic camera from going forward within the hollow middle to provide better visualization without creating extra barrier in front of the light and lenses of the camera. In one embodiment, the device comprises a camera cover configured to cover the camera and the light emitting device. The camera cover is, in one example, an endoscope cover.

In one embodiment, the endoscope device provides more privacy, thereby eliminating uncomfortable and awkward experience of the users. Further, the device allows the medical professional to look at the handheld display to monitor the pap-test procedure. In one embodiment, the protective guide makes the test procedure less invasive and less painful. Also, the chambers follow the vertically shaped entrance of vaginal canal. The protective guide is a self-testing and professional medical testing device and could include the use of a sterile medical gel lubricant to allow for easier insertions and sample collection.

In one embodiment, the device further comprises a thin flexible transparent sheath configured to cover the camera cover and a cell extraction device cover configured to cover the cell extraction device. The flexible transparent sheath is a condom covering the camera cover. In one embodiment, the thin flexible transparent sheath covers the endoscope cover, the endoscope, and endoscope cord. During the test, the cell extraction device is pushed outward from the cell extraction device cover, thereby allowing the cell extraction device brush to contact the cervix and removes/collects sample cells from the cervix, wherein the cell extraction device is then pulled back into the cell extraction device cover after sample cells are collected from the cervix. In one embodiment, the lower chamber has a punch through a very thin medical grade poly-vinyl chloride (PVC).

In one embodiment, the cell extraction device cover comprises a tunnel configured to insert the cell extraction device. The camera cover and cell extraction device cover are press fit together. In one embodiment, the protective guide further comprises at least one elastic band for holding the camera cover and the cell extraction device cover together. In one embodiment, the cell extraction device is a pap smear brush. In one embodiment, the cell extraction device is a pap smear broom. In one embodiment, the cell extraction device is a Pap smear spatula.

In one embodiment, the endoscope device is securely positioned within the upper chamber of the disposable protective guide. In one embodiment, the cell extraction device comprises a handle at one end and a brush affixed at another end. In one embodiment, the cell extraction device is slidably positioned within the lower chamber of the protective guide. In one embodiment, the cell extraction device is configured to enable a user to slide outward for positioning the brush around the user's cervix, thereby conveniently collecting a cervical cell sample.

The cervical OS is part of the female reproductive system and is located in the pelvis. It is part of the cervix, which is in the lower part of the uterus. The cervix is about two inches in length but can vary in length and width during a woman's lifetime. In one embodiment, the lower chamber is protected from vaginal fluids to avoid contamination until it reaches the OS cervical point for cell collection procedures. After reaching the point of interest, the brush is pushed forward to punch through the thin vinyl protection curtain. The brush is then turned a few times clockwise and counterclockwise to collect the cells from the surrounding tissues of the OS. In one embodiment, the brush that contains collected cells will be inserted and rinsed by inserting and swirling the spatula/brush in the solution vial vigorously for about 10 times. In one embodiment, the end of the brush tube punches through the thin vinyl protection wall. In one embodiment, the upper chamber comprises a lip stopper configured to stop the endoscopic camera from going forward with hollow middle to provide better visual without creating extra barrier in front of the light emitting device and lenses of the camera.

In one embodiment, the computing device is in communication with the endoscope via a connecting cable. In one embodiment, the connecting cable is a universal serial bus (USB) cable. In one embodiment, the computing device is in communication with the endoscope device and is configured to improve detection accuracy and visual examinations of the targeted cervical area, thereby enabling the user to accurately position the cell extraction device and comfortably collect the cervical cell sample for conducting the PAP test without the need for assistance by a gynecologist and/or a medical practitioner. In one embodiment, the device could be used in a wireless and mobile manner.

In one embodiment, the computing device comprises a processor and a memory having a software module executed by the processor. In one embodiment, the software module is at least one of a plugin component and/or a browser extension. Further, the processor is in communication with a server via a network. The computing device further comprises a database in communication with the server configured to store data related to the PAP test for the user. In one embodiment, the database is in communication with the server and the server is configured to store data related to testing documentation for patients, medical history forms & patient file database, training videos and guideline manuals, image and video file capture and storage, specimen label and laboratory requisition forms, and Health Insurance Portability and Accountability Act (HIPAA) compliant integration options for Electronic Health Record (EMR) systems.

In one embodiment, the computing device is at least anyone of a smart phone, a tablet, a computer, a laptop, a monitor, and other suitable electronic communication device that is configured to provide visual reference for the medical professionals conducting the test. In one embodiment, the device is further configured to be utilized in the early detection of chlamydia, gonorrhea, human papillomavirus (HPV), and other sexually transmitted viruses or infections (STI). In one embodiment, the device brush and camera assembly at the end piece stop the device from completely going forward or pushing through the chambers. The end-cap feature of the present disclosure helps to stop the device from being completely inserted during the pushing of the brush and applied forces. In one embodiment, the end-cap part is shaped as to the external shape of the vagina.

One aspect of the present disclosure is directed to a medical device for conducting a Papanicolaou (PAP) test, comprising: (a) a protective endoscopic catheter or protective guide having an upper chamber and a lower chamber; (b) an endoscope device having a camera and a light emitting device assembly, wherein the endoscope device is securely positioned within the upper chamber of the disposable protective guide; (c) a cell extraction device having a handle at one end and a brush affixed at another end, wherein the cell extraction device is slidably positioned within the lower chamber of the protective guide, and wherein the cell extraction device is configured to enable a user to slide outward for positioning the brush around the user's cervix, thereby conveniently collecting a cervical cell sample; and (d) a computing device in communication with the endoscope device configured to improve detection accuracy and visual examinations of the targeted cervical area, thereby enabling the user to accurately position the cell extraction device and comfortably collecting the cervical cell sample for conducting the PAP test without the need for assistance by a gynecologist and/or a medical practitioner, wherein the computing device comprises a processor and a memory having a software module executed by the processor, wherein the software module is at least one of a plugin component and/or a browser extension, wherein the processor is in communication with a server via a network, and a database in communication with the server configured to store data related PAP test for the user.

Another aspect of the present disclosure is directed to a protective guide for protecting a cell extraction device during a pap smear test, comprising: a camera configured to determine the location of the cervix; a light emitting device configured to illuminate the surfaces or spaces to view the width; a camera cover configured to cover the camera and the light emitting device; a thin flexible transparent sheath configured to cover the camera cover; and a cell extraction device cover configured to cover the cell extraction device, wherein the cell extraction device is pushed outward from the cell extraction device cover, thereby allowing the cell extraction device brush to contact the cervix and removes/collects sample cells from the cervix, wherein the cell extraction device is pulled back into the cell extraction device cover after collecting sample cells from the cervix.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION

The present invention generally relates to a gynecological medical device and more particularly relates to a medical device for enabling a woman to simply conduct a Papanicolaou (PAP) test by conveniently collecting a cervical cell sample without the need for assistance by a gynecologist or other medical practitioner.

A description of embodiments of the present invention will now be given with reference to the figures. It is expected that the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

Figure 1:
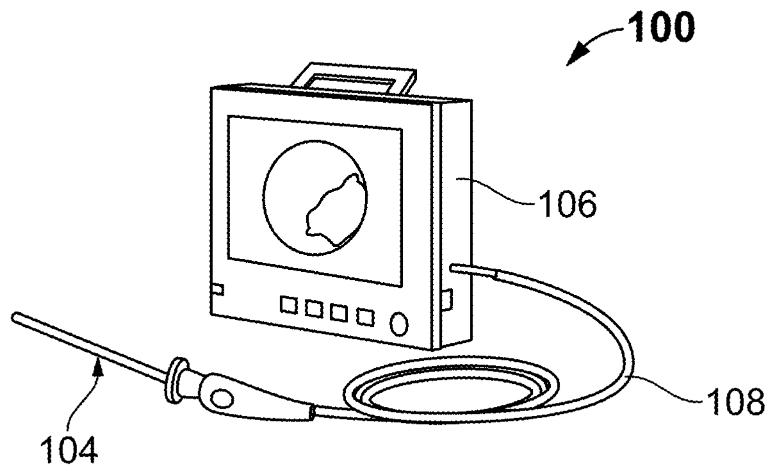
FIG. 1 exemplarily illustrates a schematic diagram of a pap smear testing device, according to an embodiment of the present invention.

Referring to FIG. 1, a schematic diagram of a pap smear test device 100, according to one embodiment of the present invention. The device 100 allows for a comfortable and efficient testing procedure, without the utilization of a speculum. The patient no longer has to experience the fear, pain, and apprehension that is commonly associated with the pap smear test. In one embodiment, the device 100 allows for mobile testing options, self-testing kits, and for an easier and quicker cell collection or gathering of a sample of cells from the cervix. In one embodiment, the device 100 is utilized for concept detection, sample collection, screening, early detection, collections of abnormal cells from the cervix, and for new testing procedures. The device 100 has the potential to positively benefit the health of millions of women worldwide and help to save many lives by enabling the early detection of cervical cancer, chlamydia, gonorrhea, human papillomavirus (HPV), and other sexually transmitted viruses or infections.

Figure 4:
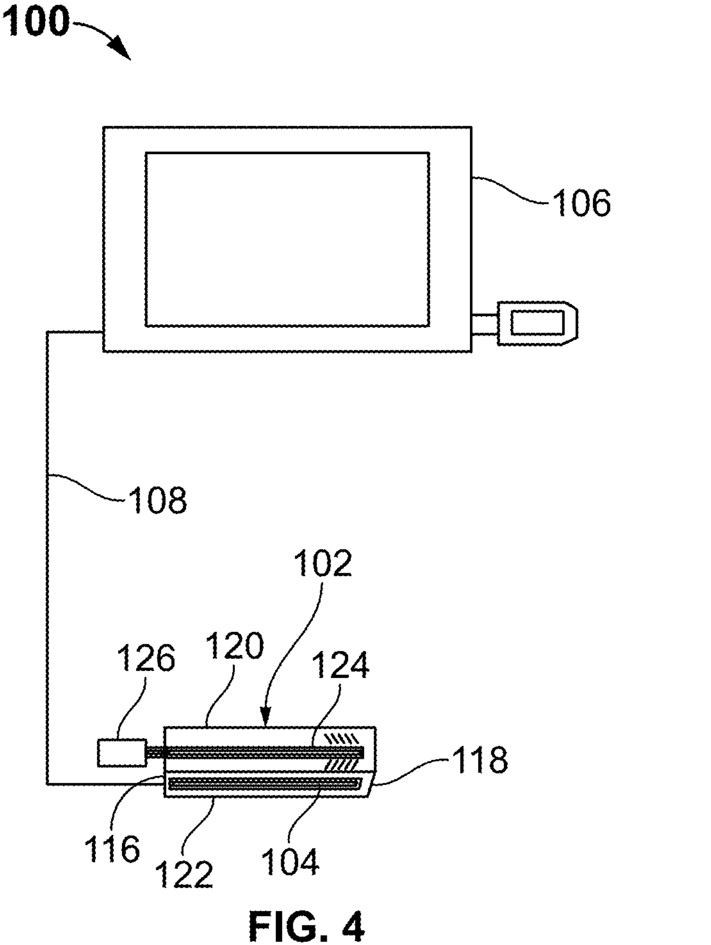
FIG. 4 exemplarily illustrates a block diagram of the device, according to an embodiment of the present invention.

In one embodiment, the device 100 comprises a protective endoscopic catheter assembly or a protective guide 102 having an upper chamber 122 and a lower chamber 120 (shown in FIG. 4). In one embodiment, the protective guide 102 is a disposable dual-chambered tube.

In one embodiment, the device 100 further comprises an endoscope or endoscopic device 104 and a computing device 106 (shown in FIG. 1). The endoscope 104 has a small a camera and a light emitting device assembly at its distal end 110 (shown in FIG. 2). In one embodiment, the light emitting device assembly comprises one or more light emitting diodes (LEDs). In an exemplary embodiment, the light emitting device assembly comprises at least 4 LEDs. In one embodiment, the device 100 involves the use of the endoscopic camera with an adjoining protective guide 102 (shown in FIG. 3).

In one embodiment, a flexible vaginal swab brush or a cell extraction device 126 (shown in FIG. 4) is inserted into the targeted cervical area via the protective guide 102 for sample cell collection. In one embodiment, the endoscope 104 is attached to the computing device 106 via a connecting cable 108 and is configured to provide visual reference for the medical professionals conducting the test. In one embodiment, the connecting cable 108 is a universal serial bus (USB) cable. In one embodiment, the computing device 106 is at least anyone of a mobile phone, smart phone, tablet, laptop, desktop, monitor, or other suitable electronic communication device configured to provide visual reference for the medical professionals conducting the test.

Figure 2:
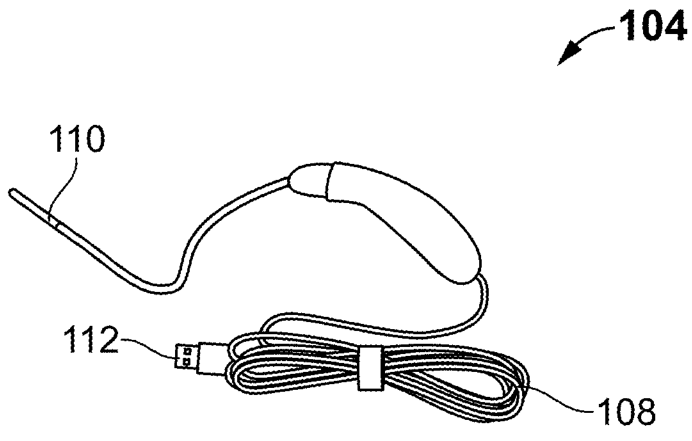
FIG. 2 exemplarily illustrates a schematic diagram of an endoscopic camera, according to an embodiment of the present invention.

Referring to FIG. 2, a schematic diagram of the endoscope 104, according to one embodiment of the present invention. The endoscope 104 includes an endoscope camera and a light emitting device at its insertion end or distal end 110. In one embodiment, the light emitting device comprises at least 4 light emitting diodes (LEDs). The LEDs are configured to illuminate the surfaces or spaces that would otherwise need to be surgically opened or enlarged to viewing width. The endoscope 104 further comprises a connecting cable 108 and a USB connection 112. In one embodiment, the endoscope 104 is connected to computing device 106 using the connecting cable 108. In one embodiment, the connecting cable 108 could be the USB cable. The widespread use of endoscope 104 could be attributed to their ease of use. In addition, the endoscope 104 is simple and inexpensive to connect with the computing device 106.

Figure 3:
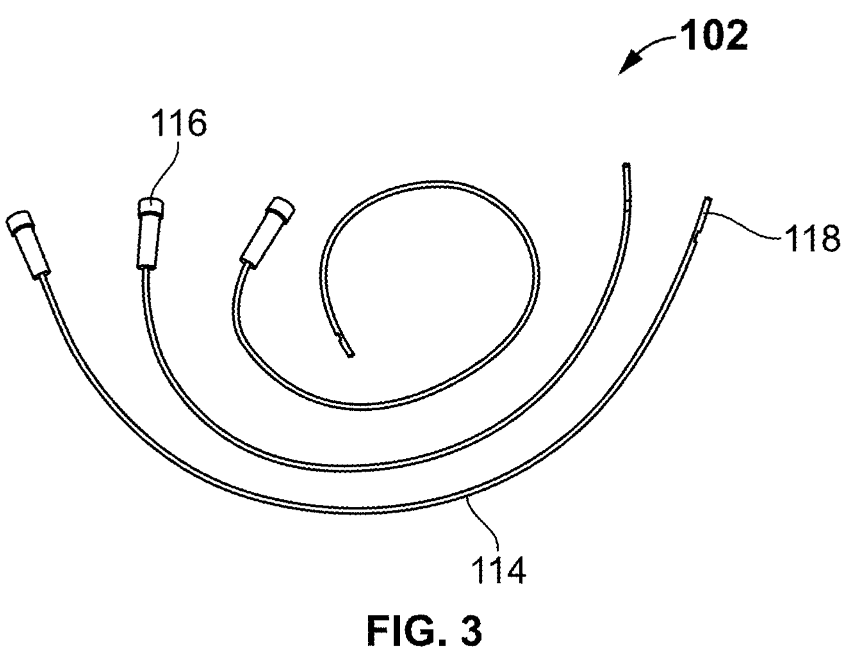
FIG. 3 exemplarily illustrates a schematic diagram of a protective catheter assembly, according to an embodiment of the present invention.

Referring to FIG. 3, a schematic diagram of the disposable protective endoscopic catheter assembly or protective guide 102, according to one embodiment of the present invention. The protective guide 102 comprises a tube guide 114 having a first end or proximal end 116 and a second end or distal end 118. The endoscope 104 is inserted into the protective guide 102 via the first end 116. The endoscope brush contacts the targeted cervix area via the second end 118. In one embodiment, the protective guide 102 has dual chambers as one piece with an existing combined vaginal swab brash assembly, which is a recommended sanitary package. In one embodiment, the protective guide 102 has an external diameter not exceeding 1 cm configured to reduce the overall diameter to help with the discomfort of larger size tubing inserted into vaginal channel.

Referring to FIG. 4, a block diagram of the pap smear test device 100, according to one embodiment of the present invention. The device 100 comprises a disposable protective endoscopic catheter assembly or a protective guide 102 having the first end 116 and the second end 118. In one embodiment, the protective guide 102 has two chambers including an upper chamber 122 and a lower chamber 120. The protective guide 102 has a maximum external diameter of 1 cm. In one embodiment, this external diameter is 0.5 cm; and in another embodiment, the external diameter is about 0.8 cm. The reduced overall diameter helps with the discomfort of larger size tubing inserted into the vaginal channel.

In one embodiment, the device 100 further comprises a camera and a light emitting device. In one embodiment, the camera and light emitting device is an endoscope 104. In one embodiment, the light emitting device comprises one or more light emitting diodes (LEDs). In an exemplary embodiment, the light emitting device comprises at least 4 LEDs. In one embodiment, the endoscope 104 is securely positioned within the upper chamber 122 of the protective guide 102. The endoscopic camera is configured to detect the location of the targeted cervix.

The light emitting device is configured to illuminate the surfaces or spaces to view the width. In one embodiment, the one or more light emitting diodes are configured to produce illumination for the camera through the endoscope to acquire video and/or image data of the user's cervical area.

In one embodiment, the protective guide 102 further comprises a camera cover to enclose or cover the camera and the light emitting device assembly. In one embodiment, the camera cover is an endoscope cover. In one embodiment, the protective guide 102 further comprises a thin flexible transparent sheath configured to cover the camera cover. In one embodiment, the thin flexible transparent sheath is a condom covering the camera cover. In one embodiment, the thin flexible transparent sheath covers the endoscope cover, the endoscope, and the endoscope cord.

In one embodiment, the upper chamber 122 is sealed at the proximal end 116 and is configured to protect the endoscopic camera, which is inserted to complete the procedure. In one embodiment, the endoscope 104 (endoscopic camera probe and LED source) could have a length of about 6 to 8 inches. In a particular embodiment, the endoscope 104 has a length of about 7 inches. The endoscope 104 comes with the connecting cable. In one embodiment, the connecting cable 108 is a USB cable. In one embodiment, the connecting cable 108 could be an optical connecting cable.

Referring to FIG. 4, in one embodiment, the device 100 further comprises a cell extraction device 124 having a handle at one end and a brush or head affixed at another end. In one embodiment, the cell extraction device 124 is slidably positioned within the lower chamber 120 of the protective guide 102. The lower chamber 120 has an opening at the proximal end 116 configured to allow the insertion of the cell extraction device 124 into it. In one embodiment, the cell extraction device 124 is configured to enable a user to slide it outward for positioning the brush around the user's cervix, thereby conveniently collecting a cervical cell sample.

The lower chamber 120 also protects the cell extraction device 124 from vaginal fluid contamination. The lower chamber 120 has an opening at the distal end 118 configured to allow the cell extraction device 124 to be pulled into the targeted cervical area to collect the sample cell. In one embodiment, the cell extraction device 124 has a flat tail handle 126 configured to rotate and twist the cell extraction device 124 in both directions for improved sample cells collection. In one embodiment, the protective guide 102 further comprises a cell extraction device cover configured to enclose the cell extraction device. In one embodiment, the cell extraction device cover comprises a tunnel configured to insert the cell extraction device 124.

In one embodiment, the camera cover and cell extraction device cover are press fit together. In one embodiment, the protective guide 102 further comprises at least one elastic band for holding the camera cover and the cell extraction device cover together. In one embodiment, the cell extraction device 124 is a pap smear brush. In one embodiment, the cell extraction device 124 is a pap smear broom. In one embodiment, the cell extraction device 124 is a pap smear spatula.

In one embodiment, the device 100 further comprises a computing device 106. The computing device is in communication with the endoscope 104 and is configured to improve the detection, accuracy and visualization of the targeted cervical area, thereby enabling the user to accurately position the cell extraction device and comfortably collect the cervical cell sample for conducting the PAP test. One of the benefits and features of the present disclosure is that the device allows for this extraction to happen without the need for assistance by a gynecologist and/or a medical practitioner and without any discomfort or pain associated with presently available devices and methods.

In one embodiment, the computing device 106 comprises a processor and a memory having a software module executed by the processor. In one embodiment, the software module is at least one of a plugin component and/or a browser extension. In one embodiment, the processor is in communication with a server via a network. In one embodiment, the computing device 106 further comprises a database in communication with the server configured to store data related to the user's PAP test results. In one embodiment, the database in communication with the server is configured to store data related to testing documentation for patients, medical history upload forms and patient file database, training videos and guideline manuals, image and video file captures and storage, specimen label and laboratory requisition form printable templates, and Health Insurance Portability and Accountability Act (HIPAA) compliant integration options for Electronic Health Record (EMR) systems.

In one embodiment, the computing device 106 is in communication with the endoscope 104 via a connecting cable 108. In one embodiment, the connecting cable 108 could be USB cable. In one embodiment, the computing device 106 could have a display or visual screen with the size of about 7.5 to 9.5 inches. The screen size enables the medical professionals to properly detect and more easily see and visualize the targeted cervical area. Also, the screen size is utilized and helpful for accurate and improved visual examinations. In one embodiment, the computing device 106 could be a mobile medically graded tablet computer with standard sized, high resolution visual screens with the size of about 7.5" to 9.5". The mobile medically graded tablet computer is used to improve the detection accuracy and provide a high-quality visual examination of the targeted vaginal area. In some embodiments, the computing device 106 could be a mobile phone, smart phone, tablet, laptop, desktop, monitor, or other suitable electronic communication device configured to provide visual reference for the medical professionals conducting the test.

In one embodiment, the computing device 106 could be installed with a customized or dedicated software application. The application could have built-in informational documentation videos and guidelines, medical history recording and patient file accessibility, images and video file storage, label and laboratory requisitions, and allow for electronic data sharing among medical professionals. In an exemplary embodiment, the application includes testing documentation for patients, medical history upload forms and patient file database, training videos and guideline manuals, image and video file capture and storage, specimen label and laboratory requisition form printable templates, Health Insurance Portability and Accountability Act (HIPAA) compliant integration options for Electronic Health Record (EMR) systems.

During the test procedure, the cell extraction device 124 is pushed outward from the cell extraction device cover so that said cell extraction device brush contacts the targeted cervix and removes cells from the cervix. Once the cells have been removed from the cervix, the cell extraction device 124 is then pulled back into the cell extraction device cover. The removed sample cells are placed on a glass slide that sent to the laboratory for testing to detect abnormalities.

In one embodiment, the device 100 is available as a self-test kit. The self-test kit comprises an endoscopic camera and cable, two disposable catheter assemblies, lubricating jelly, packet-sterile, latex-free surgical gloves, and cell preservation solution, cell collection bottle including requisitions, and specimen transport bags. These components are packed in vacuumed sealed sanitized packaging. The kit has a directional app or YouTube download to show how to use the device to collect samples by the user and without any other third party present, and also provide instructions on how to return the specimen back to the lab for further testing.

Figure 5:
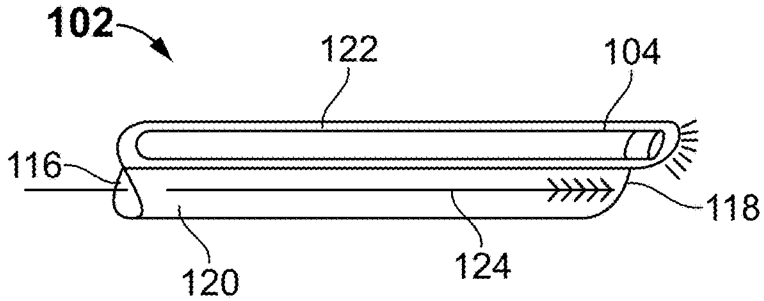
FIG. 5 exemplarily illustrates a perspective view of the protective guide provided with the endoscope and cell extraction device, according to an embodiment of the present invention.

Referring to FIG. 5, a perspective view of the protective endoscopic catheter or protective guide 102 provided with the endoscope device 104 and the cell extraction device 124 in one embodiment is disclosed. In one embodiment, the protective guide 102 comprises a lower chamber 120 and an upper chamber 122. In one embodiment, the endoscope device 104 comprises a camera and a light emitting device assembly at its distal end 110. The endoscope device 104 is securely positioned within the upper chamber 122 of the protective guide 102.

The protective guide 102 has a proximal end 116 and a distal end 118. In one embodiment, the cell extraction device 124 is slidably positioned within the lower chamber 120 of the protective guide 102, via the proximal end 116. In one embodiment, the cell extraction device 124 is configured to enable the user to slide outward at the distal end 118 for positioning the brush 128 (shown in FIG. 10) around the user's cervix, thereby conveniently allowing for a cervical cell sample to be collected for the PAP test. In one embodiment, the protective guide 102 has a length of about, but not limited to, 15 mm. In one embodiment, the inside diameter of the upper chamber 122 is about, but not limited to, 7 mm. The average depth of a vagina is about 3 inches to about 7 inches (approximately 7.6-17.7 cm). It is not necessary to make different sizes as the camera to guide the individual to reach the end of vaginal canal. The length is suited to reach the shorter length of travel with a few inches sticking out or end with maximum length of travel.

Figure 6:
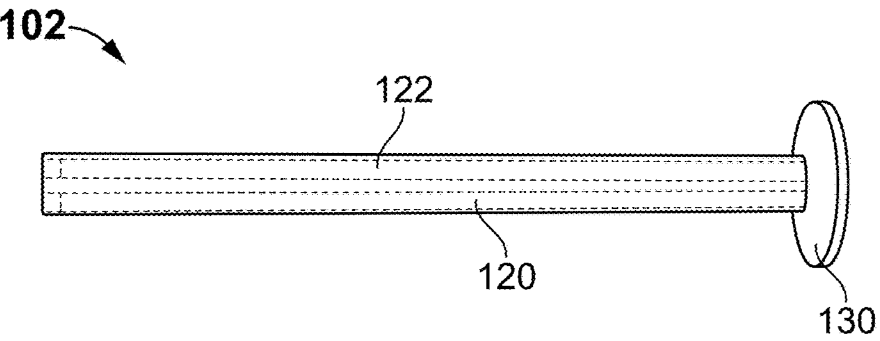
FIG. 6 exemplarily illustrates a side view of the protective guide, according to an embodiment of the present invention.
Figure 7:
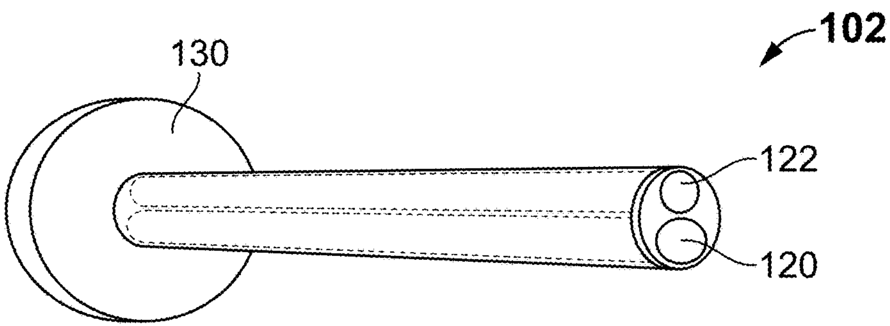
FIGS. 7 and 8 exemplarily illustrate perspective views of the protective guide, according to an embodiment of the present invention.
Figure 8:
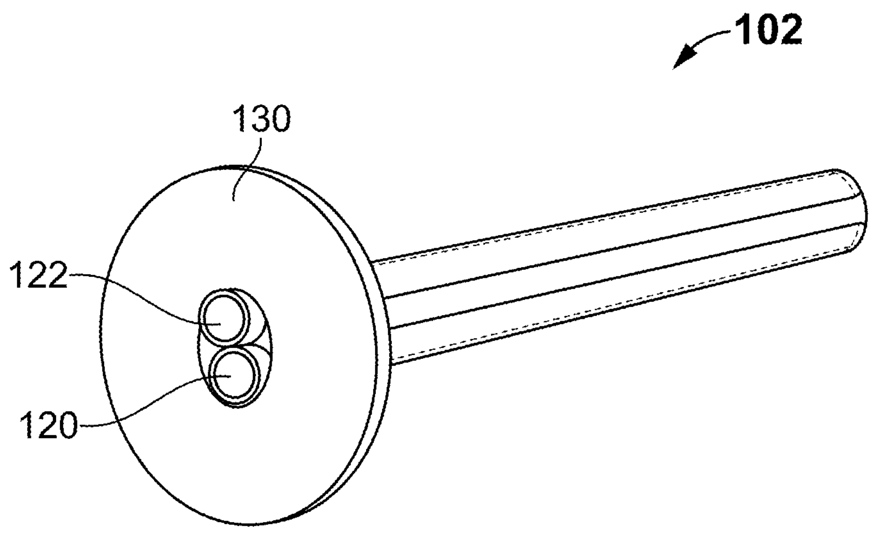

Referring to FIGS. 6-8, a side view and perspective views of the protective endoscopic catheter or protective guide 102 in one embodiment is disclosed. In one embodiment, the protective guide 102 comprises at least two chambers i.e., a lower chamber 120 and an upper chamber 122. In one embodiment, the protective guide 102 could be a disposable dual-chambered tube. In one embodiment, the lower chamber 120 is configured to receive the cell extraction device 124 and the upper chamber 122 is configured to receive the endoscope device 104. In one embodiment, the protective guide 102 has a maximum external diameter of about 1 cm.

Figure 9:
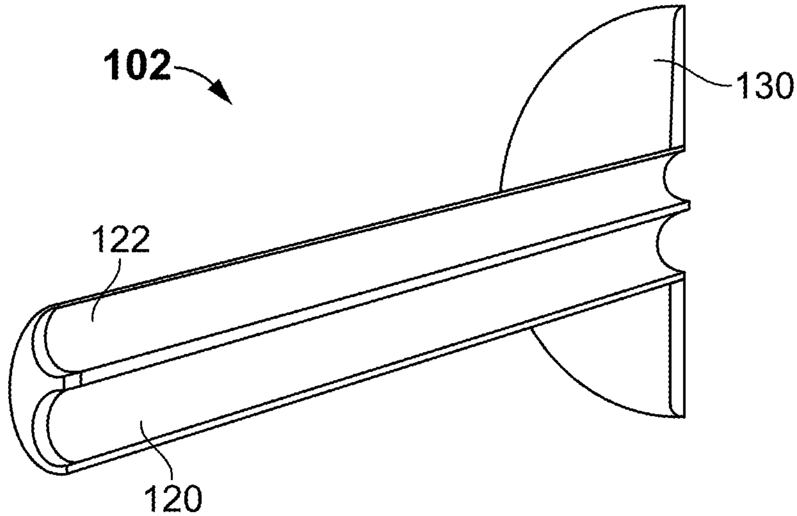
FIG. 9 exemplarily illustrates a cut-sectional view of the protective guide, according to an embodiment of the present invention.

Referring to FIG. 9, a cut-sectional view is shown of the protective guide 102 according to one embodiment of the present invention. In one embodiment, a disk 130 is securely affixed to one end of the protective guide 102. In one embodiment, the disk 130 has a diameter of about 40 mm.

In one embodiment, another end of the protective guide 102 has a diameter of about 14 mm. In one embodiment, the protective guide 102 has a length of about 175 mm. The ideal length of the protective guide 102 is measured from the tip to the stopper cap and the end. The length of the protective guide 102 is no longer than 7 inches. In addition, the protective guide 102 is explored with slight upward curb to consider the inside shape of vagina.

Figure 10:
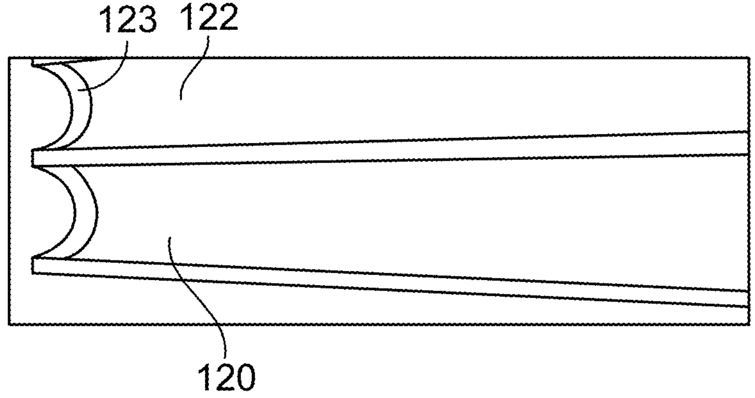
FIG. 10 exemplarily illustrates an enlarged view of the protective guide, according to an embodiment of the present invention.

In one embodiment, the protective guide 102 has a lower chamber 120 and an upper chamber 122. FIG. 10 exemplarily illustrates an enlarged view of the cut-sectional protective guide 102, according to one embodiment of the present invention. In one embodiment, the upper chamber has a lip stopper 123. In one embodiment, the lip stopper 123 is configured to stop the endoscopic camera from going forward with hollow middle to provide better visualization without creating an extra barrier in front of the light and lenses of the camera. In one embodiment, the lower chamber has a punch through thin medical grade poly-vinyl chloride (PVC).

In one embodiment, the lower chamber is protected from vaginal fluids to avoid contamination until it reaches the OS cervical point for cell collection procedures. After reaching the ideal point of interest, the brush will be pushed forward to punch through the thin vinyl protection curtain. The brush is then turned a few times clockwise and counter-clockwise to collect the cells from the surrounding tissues of the OS. In one embodiment, the brush/spatula that contains the collected cells is inserted and rinsed in the cell collection vial for about 10 times or about five minutes. In one embodiment, the lower chamber 120 of the protective guide 102 has a diameter of about 5.7 mm and the upper chamber 122 has a diameter of about 5.5 mm. In one embodiment, the protective guide 102 is made of, for example, a transparent material. The protective guide 102 could be made of an opaque material.

Figure 11:
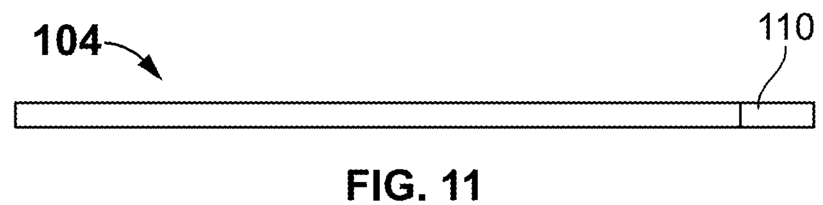
FIG. 11 exemplarily illustrates a side view of the endoscope device, according to an embodiment of the present invention.

Referring to FIG. 11, a side view of the endoscope device 104 in one embodiment is disclosed. In one embodiment, the endoscope device 104 is used for screening the user's cervix or cervical area using the computing device 106 (shown in FIG. 4). In one embodiment, the endoscope device 104 comprises a camera, one or more light emitting diodes (LEDs), and at least one USB port connection. In one embodiment, the camera could be, but is not limited to, a USB endoscope camera. In one embodiment, the endoscope device 104 is inexpensively and simply connected to the computing device 106 or a large screen via the USB port connection or a cable 108 (shown in FIG. 4), for example, a video cable.

The location of the user's cervix could be determined by utilizing the camera. In one embodiment, the one or more light emitting diodes (LEDs) are configured to produce illumination for the camera through the endoscope device 104 to acquire video and/or image data of the user's cervical area. In one embodiment, the endoscope device 104 has a diameter of about, but is not limited to, 5 mm and the length ranges from about 8.5 mm to about 21.5 mm.

Figure 12:
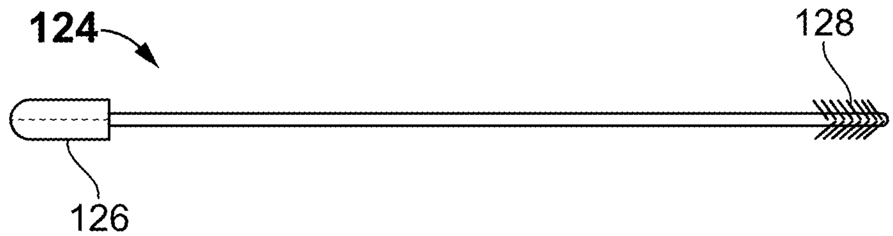
FIG. 12 exemplarily illustrates a side view of the cell extraction device, according to an embodiment of the present invention.

Referring to FIG. 12, the cell extraction device 124 of the present invention in one embodiment is disclosed. In one embodiment, the cell extraction device 124 comprises a handle 126 at one end and a brush 128 affixed at another end. In one embodiment, the handle 126 could be a flat tail handle in order to rotate and twist the cell extraction device 124 in both directions for efficiently collecting the cervical cell sample. In one embodiment, the cell extraction device 124 is slidably positioned within the upper chamber 122 of the protective guide 102. The cell extraction device 124 is configured to enable the user to slide it outward for positioning the brush 128 around the user's cervix, thereby conveniently collecting the cervical cell sample without the need for assistance by a gynecologist or other medical practitioner. In one embodiment, the protective guide 102 will guide and protect the brush 128 from vaginal fluid contamination.

The cell extraction device 124 is pushed outward from the upper chamber 122 of the protective guide 102, so that said brush 128 contacts the user's cervix and removes sample cells from the cervix. The cell extraction device 124 is pulled back into the upper chamber 122 of the protective guide 102 after the sample cells have been removed from the user's cervix. In one embodiment, the cell extraction device 124 has a length of about, 8 inches. In one embodiment, the handle 126 has a length of about one inch. The one size protective guide 102 with endoscopic camera of the instant pap-test testing device easily acts as a guide to the end of the vaginal canal, regardless of the length. The device could be sticking out a few inches for a shorter or minimum length, whereas the device is fully inserted for the maximum length depending on the need.

According to the present invention, the device provides lower procedure costs. The device makes the test procedure less invasive and painful. The device shortens the procedure time-frame and increases the efficiency. Also, the device makes the testing process more accurate. It makes testing equipment more accessible. In addition, it allows for mobile testing options, self-testing kits, easier and quicker cell collection of a sample of cells from the cervix, digital visualizations to allow closer examination and added privacy, video recording and collecting visual data, with training applications and software dedicated to testing procedures.

Advantageously, all medical professionals are capable of conducting the test using the device. The device has a smaller insertion diameter for total catheter assembly. It could also be used as self-testing kit, providing for a more accurate and robust test than existing devices. The efficiency and simplicity of the testing process allows for more tests to be scheduled per day than traditional pap-tests. Medical professionals without a gynecological background can be efficiently and easily trained in this testing method to complete the sample collection procedure. Indeed, women with no training are able to follow basis instructions and to use this device in the privacy of their homes and or in locations where no other person is present. The present disclosure allows for more accessibility by the everyday consumer to medical professionals, laboratories, and medical technicians to do the test based on the sample taken by the everyday consumer. In addition, mobile nurses and trained staff could reach patients anywhere, lending this device especially useful in locations and countries where access to healthcare and medical diagnostics is very limited.

Further, the device could potentially create a new market profitability for medical professionals. It reduces the testing cost so that more women can do the testing. It could also be expanded for all medical centers, including for example, specialty doctor offices. The device is affordable enough for an independent, traveling medical professional to provide in-home testing to their patients. Also, mobile medical practices could purchase several devices and provide each of their mobile professionals with kits for use in the field.

The present disclosure will allow access and testing to a much wider and larger group of women in the U.S. and worldwide and is likely to garner support from world health organizations and women health associations. There will be revenue from disposable catheter assembly and self-testing kits. Laboratories will be able to establish partnerships with medical Offices and receive self-tested specimens to process test results, generating revenue for the lab and cutting costs for the medical practices. The self-test will include profit margins from laboratory as well for distributions.

As such, one aspect of the present disclosure is directed to a medical device for conducting a Papanicolaou (PAP) test, comprising: (a) a protective endoscopic catheter or protective guide having an upper chamber and a lower chamber; (b) an endoscope device having a camera and a light emitting device assembly, wherein the endoscope device is securely positioned within the upper chamber of the disposable protective guide; (c) a cell extraction device having a handle at one end and a brush affixed at another end, wherein the cell extraction device is slidably positioned within the lower chamber of the protective guide, and wherein the cell extraction device is configured to enable a user to slide outward for positioning the brush around the user's cervix, thereby conveniently collecting a cervical cell sample; and (d) a computing device in communication with the endoscope device configured to improve detection accuracy and visual examinations of the targeted cervical area, thereby enabling the user to accurately position the cell extraction device and comfortably collecting the cervical cell sample for conducting the PAP test without the need for assistance by a gynecologist and/or a medical practitioner, wherein the computing device comprises a processor and a memory having a software module executed by the processor, wherein the software module is at least one of a plugin component and/or a browser extension, wherein the processor is in communication with a server via a network, and a database in communication with the server configured to store data related PAP test for the user.

In one embodiment, the protective guide is a disposable dual-chambered tube. In another embodiment, the light emitting device assembly comprises one or more light emitting diodes (LEDs). In one embodiment, the one or more light emitting diodes are configured to produce illumination for the camera through the endoscope to acquire video and/or image data of the user's cervical area. In one embodiment, the computing device is in communication with the endoscope via a universal serial bus (USB) cable. In another embodiment, the database in communication with the server is configured to store data related to testing documentation for patients, medical history upload forms & patient file database, training videos and guideline manuals, image and video file capture and storage, specimen label and laboratory requisition form printable templates, and Health Insurance Portability and Accountability Act (HIPAA) compliant integration options for Electronic Health Record (EMR) systems.

In one embodiment, the computing device is at least anyone of a smart phone, a tablet, a computer, a laptop, a monitor, and other suitable electronic communication device configured to provide visual reference for the medical professionals conducting the test. In another embodiment, the medical device is further configured to utilize for early detection of chlamydia, gonorrhea, human papillomavirus (HPV), and other sexually transmitted viruses or infections (STI). In one embodiment, the protective guide has a maximum external diameter of less than 1 cm.

Another aspect of the present disclosure is directed to a protective guide for protecting a cell extraction device during a pap smear test, comprising: a camera configured to determine the location of the cervix; a light emitting device configured to illuminate the surfaces or spaces to view the width; a camera cover configured to cover the camera and the light emitting device; a thin flexible transparent sheath configured to cover the camera cover; and a cell extraction device cover configured to cover the cell extraction device, wherein the cell extraction device is pushed outward from the cell extraction device cover, thereby allowing the cell extraction device brush to contact the cervix and removes/collects sample cells from the cervix, wherein the cell extraction device is pulled back into the cell extraction device cover after collecting sample cells from the cervix.

In one embodiment, the camera and light emitting device is an endoscope. In another embodiment, the camera cover is an endoscope cover. In one embodiment, the flexible transparent sheath is a condom covering the camera cover. In one embodiment, the thin flexible transparent sheath covers the endoscope cover, the endoscope, an endoscope cord. In one embodiment, the cell extraction device cover comprises a tunnel configured to insert the cell extraction device. In another embodiment, the camera cover and cell extraction device cover are press fit together. In a related embodiment, the protective guide further comprises at least one elastic band for holding the camera cover and the cell extraction device cover together. In one embodiment, the cell extraction device is a pap smear brush. In another embodiment, the cell extraction device is a pap smear broom. In yet another embodiment, the cell extraction device is a pap smear spatula.

The foregoing description comprise illustrative embodiments of the present invention. Having thus described exemplary embodiments of the present invention, it should be noted by those skilled in the art that the within disclosures are exemplary only, and that various other alternatives, adaptations, and modifications may be made within the scope of the present invention. Merely listing or numbering the steps of a method in a certain order does not constitute any limitation on the order of the steps of that method.

Many modifications and other embodiments of the invention will come to mind to one skilled in the art to which this invention pertains having the benefit of the teachings presented in the foregoing descriptions. Although specific terms may be employed herein, they are used only in generic and descriptive sense and not for purposes of limitation. Accordingly, the present invention is not limited to the specific embodiments illustrated herein. While the above is a complete description of the preferred embodiments of the invention, various alternatives, modifications, and equivalents may be used. Therefore, the above description and the examples should not be taken as limiting the scope of the invention, which is defined by the appended claims.

The invention claimed is:

1. A medical device for conducting a Papanicolaou (PAP) test comprising:

(a) an elongated protective guide having a first elongated chamber and a second elongated chamber, the first elongated chamber and the second elongated chamber extending from a proximal end of the elongated protective guide to a distal end of the elongated protective guide, wherein the first elongated chamber and the second elongated chamber are integrally formed within the elongated protective guide;

(b) a device positionable within the first elongated chamber of the elongated protective guide, the device having a camera and a light emitting device assembly, wherein the first elongated chamber comprises a lip stopper, and wherein the device contacts the lip stopper to prevent the device from moving out of the first elongated chamber, and wherein the lip stopper comprises a hollow middle that avoids creating a barrier in front of the camera and the light emitting device assembly of the device to provide better visualization of a targeted cervical area by the camera;

(c) a cell extraction device slidably positioned within the second elongated chamber of the protective guide, the cell extraction device having a handle at a first end and one of a cell-extraction brush or a cell-extraction spatula at a second end, opposite the first end, wherein the second elongated chamber comprises a displaceable seal positioned within the second elongated chamber, the displaceable seal configured to protect the cell extraction device from contamination during insertion of the elongated protective guide, the displaceable seal being displaceable by advancement of the cell extraction device to enable the cell extraction device to contact the cervix;

(d) a computing device in communication with the device, the computing device having a processor and a memory having a software module executed by the processor; and (e) a display in communication with the computing device, the display adapted to display the targeted cervical area imaged by the camera of the device to assist the user in positioning the one of the cell-extraction brush and the cell-extraction spatula at a transformation zone of the cervix.

2. The medical device of claim 1, wherein the protective guide is a disposable protective guide.

3. The medical device of claim 1, wherein the light emitting device assembly comprises at least four light emitting diodes configured to produce illumination of the targeted cervical area.

4. The medical device of claim 1, wherein the computing device is in communication with the device via a universal serial bus (USB) cable.

5. The medical device of claim 1, wherein the processor is in communication with a database configured to store data generated by the medical device, the data comprising at least (i) image and video file data of the targeted cervical area captured by the camera during the PAP test, and (ii) specimen label and laboratory requisition form printable templates for the PAP test specimen collected by the cell extraction device.

6. The medical device of claim 1, wherein the computing device is one or more of a smart phone, a tablet, a computer, a laptop, a monitor, and other suitable electronic communication devices configured to provide visual reference for medical professionals conducting the PAP test.

7. The medical device of claim 1, wherein the medical device is used in the process of detecting at least one of chlamydia, gonorrhea, human papillomavirus (HPV), and other sexually transmitted viruses or infections.

8. The medical device as recited in claim 1, wherein the elongated protective guide comprises a cylindrical guide having a substantially constant external diameter from the proximal end to the distal end.

9. The medical device as recited in claim 8, wherein the substantially constant external diameter does not exceed 1 centimeter.

10. The medical device as recited in claim 8, wherein the substantially constant external diameter does not exceed 0.5 centimeters.

11. The medical device as recited in claim 1, wherein the lip stopper is located adjacent the distal end of the elongated protective guide.

12. The medical device as recited in claim 11, wherein the lip stopper located adjacent the distal end of the elongated protective guide positions the camera of the device adjacent the distal end of the elongated protective guide.

13. The medical device as recited in claim 1, wherein the elongated protective guide comprises an elongated housing having the first elongated chamber and the second elongated chamber.

14. The medical device as recited in claim 1, wherein the first elongated chamber and the second elongated chamber each comprise a substantially uniform inside dimension from the proximal end of the elongated protective guide to a distal end of the elongated protective guide.

* * * * *